(12) United States Patent
Stvartak et al.

(10) Patent No.: US 6,601,272 B2
(45) Date of Patent: Aug. 5, 2003

(54) DENTAL HYGIENE SYSTEM HANDLE

(75) Inventors: Christopher Stvartak, Skokie, IL (US); Kevin G. Yost, Winnetka, IL (US)

(73) Assignee: John O. Butler Company, Chicago, IL (US)

(*) Notice: Subject to any disclaimer, the term of this patent is extended or adjusted under 35 U.S.C. 154(b) by 0 days.

(21) Appl. No.: 09/915,081

(22) Filed: Jul. 25, 2001

(65) Prior Publication Data

US 2002/0170145 A1 Nov. 21, 2002

Related U.S. Application Data

(63) Continuation-in-part of application No. 09/075,062, filed on May 8, 1998, now abandoned.

(51) Int. Cl.[7] .................................................. A46B 5/02
(52) U.S. Cl. ........................ 16/430; 15/167.1; 132/309; 132/200
(58) Field of Search ................................ 132/308, 309, 132/328, 200; 15/167.1, 167.2; 16/430; D4/104, 110, 112, 138

(56) References Cited

U.S. PATENT DOCUMENTS

| | | | | |
|---|---|---|---|---|
| D110,185 S | * | 6/1938 | Lukenbill | D4/104 |
| D110,186 S | * | 6/1938 | Lukenbill | D4/104 |
| 4,517,701 A | * | 5/1985 | Standford, Jr. | 15/167.1 |
| D285,263 S | * | 8/1986 | Hill | D4/104 |
| 5,339,482 A | * | 8/1994 | Desimone et al. | 15/167.1 |
| D351,733 S | * | 10/1994 | Maekawa et al. | D4/104 |
| D360,984 S | * | 8/1995 | Sullivan, IV | D4/104 |
| 5,465,449 A | * | 11/1995 | Lewkowicz | 15/167.1 |
| 5,530,989 A | * | 7/1996 | Remmert et al. | 16/430 |
| 5,781,963 A | * | 7/1998 | Maru et al. | 16/430 |
| 5,864,915 A | * | 2/1999 | Ra | 15/167.1 |
| 5,875,510 A | * | 3/1999 | Lamond et al. | 15/167.1 |

* cited by examiner

Primary Examiner—Todd E. Manahan
(74) Attorney, Agent, or Firm—Michael, Best & Friedrich LLC

(57) ABSTRACT

A dental hygiene system handle including a proximal grip section, a central control section, and a distal brush section, the central control section including four elastomeric lands for receiving the thumb and forefinger of a user on opposite sides of the central control section.

24 Claims, 4 Drawing Sheets

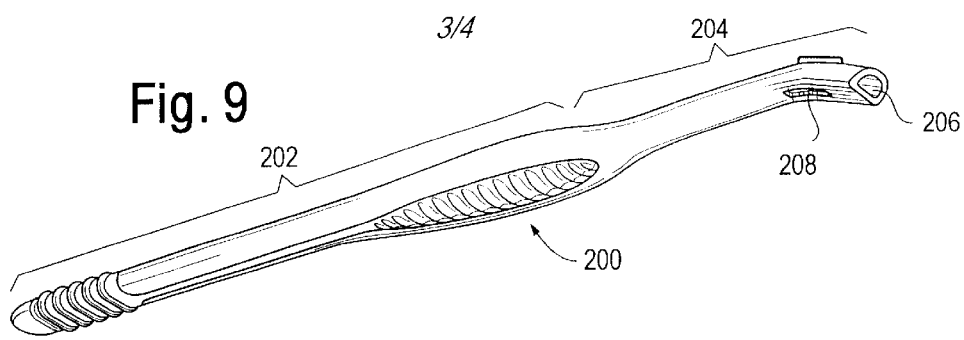
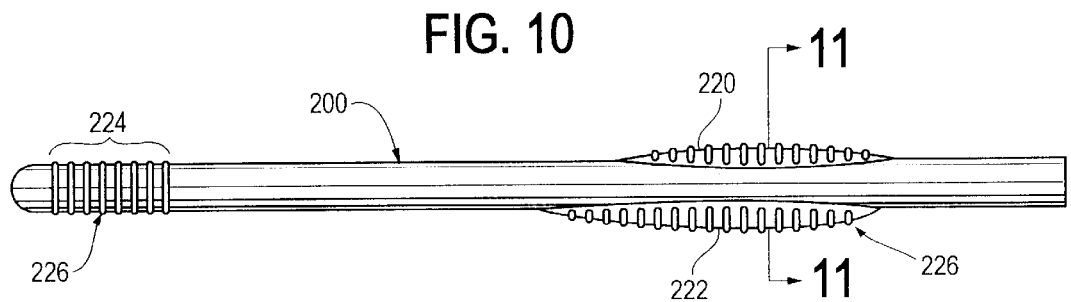
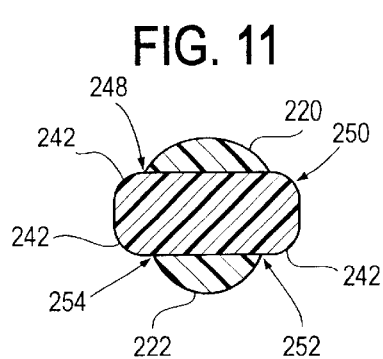
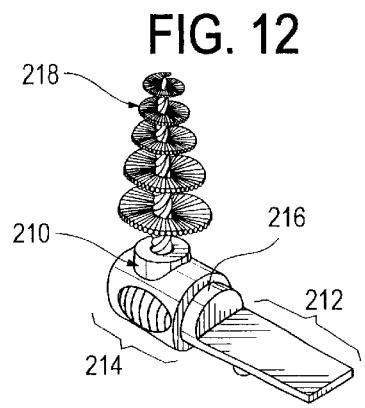
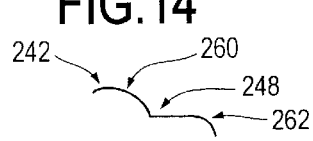
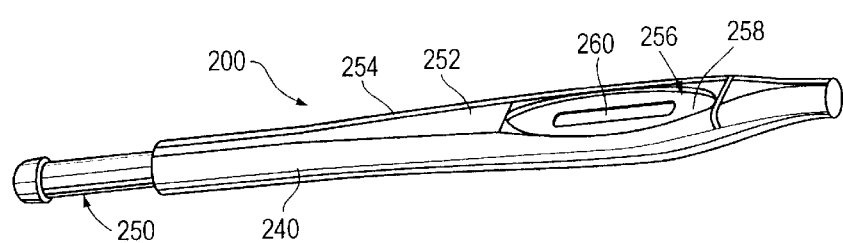

DENTAL HYGIENE SYSTEM HANDLE

This application is a continuation-in-part of U.S. patent application Ser. No. 09/075,062, filed May 8, 1998, which is now abandoned.

FIELD OF THE INVENTION

The present invention relates generally to dental hygiene systems intended for manual operation and more particularly to improved dental hygiene handles designed for conveniently manipulating a variety of different dental cleaning or stimulating elements. The present invention includes a particularly important improvement to conventional unitary toothbrushes.

BACKGROUND OF THE INVENTION

Various devices are known in the art for cleaning and stimulating the teeth and gums to maintain good dental hygiene. The most ubiquitous such device is the conventional toothbrush. Another popular cleaning and stimulating device is an interproximal toothbrush such as one of the many different interproximal toothbrushes which are available from John O. Butler Company of Chicago, Ill. Still other types of commonly used cleaning and stimulating devices are rubber stimulators, picks, flossers and even small dental mirrors which aid in monitoring inaccessible areas in the mouth.

These cleaning and stimulating devices may be unitary, comprising a handle and a brush or other cleaning or stimulating element mounted directly in the distal end of the handle. Alternatively, these cleaning and stimulating devices may be removably mounted to the handle. Examples of known approaches to removable mountings of interproximal brushes, rubber stimulators, picks, flossers, and small dental mirrors may be found in U.S. Pat. Nos. 5,934,295, 5,758,382, and 5,027,467, which are incorporated by reference.

In using all such dental cleaning and stimulating devices, it is important that the handle in which the devices are held or mounted be easy and comfortable to grip. It is also important that the handle be easy to manipulate. As explained below, in the case of conventional toothbrushes, it is particularly important that the handle be easy to rotate back and forth about its longitudinal axis.

The significance of the handle design is particularly apparent when the Bass method of tooth brushing with a conventional toothbrush is considered. This technique is the most widely recommended method for using a toothbrush to remove plaque from the gingival sulcus and from the exposed surfaces of the teeth. The Bass method requires that the bristles of the toothbrush head be positioned along the gum line at approximately a 45° angle, with at least one row of bristles nestled below the gum line. With the brush head oriented in this way, it is gently moved back and forth in short strokes so that bristles in the gingival sulcus loosen and remove plaque which is present there while the rest of the bristles brush and massage the exposed surface of the gum and clean the exposed tooth surfaces. The bristles are then swept away from the gumline and the brush head lifted away and repositioned to perform the same process with adjacent teeth and gums. An important objective of this technique is to reduce targeted pathogenic organisms found in the gingival sulcus in order to, inter alia, minimize or eliminate gingival inflammation and bleeding.

It is therefore an object of this invention to provide a toothbrush handle that is easy to manipulate generally, and that is easy to rotate about its longitudinal axis.

It is another object of this invention to provide a toothbrush handle that is well adapted for use in the Bass method of toothbrushing.

It is a further object of the present invention to provide a dental hygiene handle which can be easily and conveniently shifted to a variety of different positions to enable the user to conveniently manipulate a variety of different dental cleaning and stimulating devices.

Yet another object of the present invention is to provide a handle for use in dental hygiene systems which is particularly comfortable to use in a variety of different positions.

These and other objects and advantages of the invention will appear hereinafter.

SUMMARY OF THE INVENTION

The present invention, in a preferred embodiment, accomplishes the foregoing objects by providing a dental hygiene system handle well adapted for comfortably gripping and manipulating and rotating about its longitudinal axis, including a proximal grip section, a distal brush section and, therebetween, a central control section. The central control section has four elastomeric lands for receiving the thumb and forefinger of a user on opposite sides of the central control section. The lands meet each other at the outer surface of the central control section at angles from about 25° to 65°, and preferably at an angle of about 45°.

The dental hygiene system handle typically will have a toothbrush head with bristles at its distal end. The handle may be unitary, with the toothbrush head being integral with the rest of the handle and the bristles being mounted in the head. Alternatively, the toothbrush head is removably mounted to the handle.

The grip of the proximal grip section is generally ellipsoidal in shape, rounded at its proximal tip and bulging outwardly as the contour of the grip moves distally to its maximum radial divergence. The central control section necks down and then diverges outwardly in a smooth curved contour to a pair of peaks near the distal end of the control section. Within the area of the peaks are lands for the placement of a user's thumb meeting at the outer surface of the central control section at an angle of about 45°.

The lands may be of a generally inverted teardrop shape, with a larger rounded end of the teardrop oriented generally toward the distal end of the central control section and a smaller, narrower rounded end of the teardrop oriented generally toward the proximal end of the central control section. Also, the lands may include a raised design.

In one particularly preferred embodiment, the handle comprises a rigid base member that is selectively overmolded with elastomer. In this embodiment, the rigid base member includes an overmolding area extending from just distal to the end of the handle comprising a slot in the top of the base member that extends below the handle along its proximal and central control sections to form a half-moon cut-away profile on the bottom of the rigid base member. The half-moon cut-away profile is flanked by a pair of ledges and the cut-away profile runs from the bottom of the handle into another slot that encircles the neck of the distal brush section of the rigid base member.

Finally, a through-slot is formed in the control section and a blind slot is formed in the proximal section of the handle to help anchor the elastomer to the rigid base member. Elastomer is provided at the top of the handle in the proximal grip section extending to and running along the bottom of the handle in the central control section. The remaining sections of the handle comprise exposed portions of the rigid base member.

The invention also comprises a method of brushing the teeth by a user by providing a dental hygiene system handle as described above, gripping with the three lower fingers curled around and holding the ellipsoidal proximal grip section while the central control section is held between the forefinger and the thumb. The user then moves the handle to position the brush bristles along the gum line in one quadrant of the mouth, at approximately a 45° angle, with at least one row of bristles nestled below the gum line, gently moving the handle back and forth so that bristles in the user's gingival sulcus loosen and remove plaque present there while the rest of the bristles brush and massage the exposed surface of the gum and clean the exposed tooth surfaces.

When it is desired to move to another quadrant, the user lifts the brush bristles away and rotates the brush handle 90° or 180° along its longitudinal axis to properly position the bristles at a new location at approximately a 45° angle, with at least one row of bristles nestled below the gum line.

The above as well as other objects and advantages of the invention will become apparent from the following detailed description of the preferred embodiments in which reference is made to the accompanying drawings.

BRIEF DESCRIPTION OF THE DRAWINGS

FIG. 9 is a perspective view of a handle in accordance with the present invention adapted to accept carrying members holding a variety of different cleaning and stimulating devices;

FIG. 10 is a front elevation view of the handle of FIG. 9;

FIG. 11 is a cross-sectional view of the handle of FIGS. 9 and 10 taken along lines 11—11;

FIG. 12 is an enlarged perspective view of a carrying member intended to be inserted into the handle of FIG. 9;

FIG. 13 is perspective view of the rigid base member of FIG. 9, without the elastomeric portions appearing in FIGS. 9 and 10;

FIG. 14 is an enlarged partial diagrammatic view of selected features of the gripping section;

DETAILED DESCRIPTION OF A PREFERRED EMBODIMENT

Figure 1:
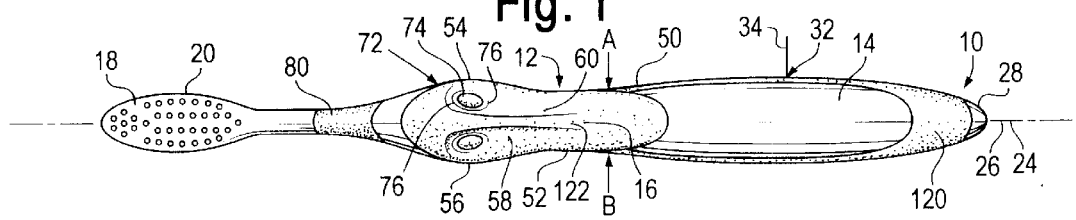
FIG. 1 is a top plan view of a handle in accordance with the present invention.
Figure 2:
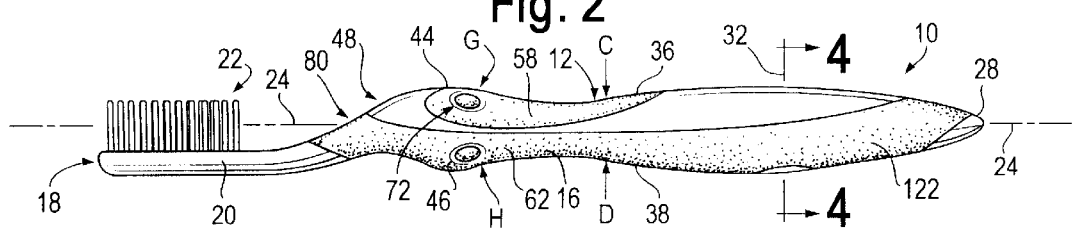
FIG. 2 is a side elevation view of a handle in accordance with the present invention.
Figure 3:
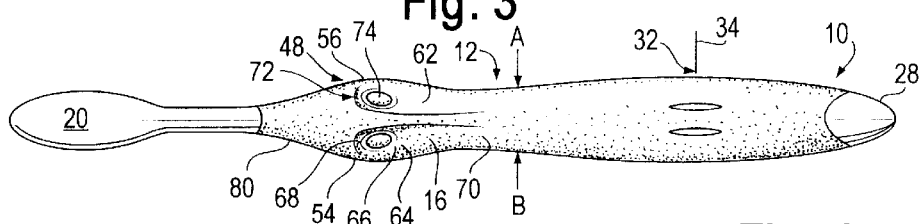
FIG. 3 is a bottom plan view of a handle in accordance with the present invention.

Referring now to the drawings, where like reference numerals have been used to designate like or similar elements, FIGS. 1, 2, and 3 are respectively top plan, side elevation, and bottom plan views of a toothbrush 10 in accordance with the present invention. Toothbrush 10 includes a unitary handle 12 having a proximal grip section 14, a central control section 16, and a distal brush section 18.

Distal brush section includes a toothbrush head 20 having a plurality of bristles 22. These bristles may be upstanding and of equal length across the toothbrush head, as illustrated in FIG. 2. Or, they may be of varying lengths, angled, feathered, etc., as discussed, for example, in U.S. patent application Ser. No. 09/496,696, filed Feb. 2, 2000, which is incorporated by reference. Also, the toothbrush head may be removable, as explained below in regard to the embodiment of FIGS. 10–13.

Proximal grip section 14 of the toothbrush handle is generally ellipsoidal in shape. In other words, the proximal section overall is a solid generated by the revolution about the longitudinal axis 24 of the toothbrush of an ellipse with its major axis 26 lying on the longitudinal axis of the handle. As can be seen in FIGS. 1–3, ellipsoidal proximal section 14 is rounded at its proximal tip 28, bulges outwardly as the contour of the grip moves distally to its maximum radial divergence at 32 along the minor axis 34 of the ellipse generating the ellipsoidal shape. The contour then blends into the central control section 16 along a cross-sectional portion of the handle defined by points A, B, C, and D.

As best seen in FIG. 2, central control section 16 has a complex shape which begins to neck down along contour lines 36 and 38 at points C and D in FIG. 2 and then diverges outwardly in a smooth curved contour at G and H to a pair of primary peaks 44 and 46 near the distal end 48 of the control section. In the plan views of FIGS. 1 and 3, at points A and B, the control section necks in only slightly along contour lines 50 and 52, and then diverges outwardly to a pair of secondary peaks 54 and 56 at the distal end 48 of the control section.

Figure 4:
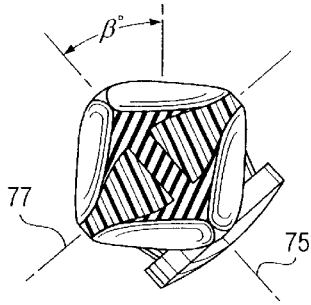
FIG. 4 is a cross-sectional view of the handle of the invention taken along lines 4—4 of FIG. 2.

The portions of the control section between contour lines 36, 50, 38, and 52 comprise lands 58, 60, 62, and 64 which meet each other at angles from about 25° to 65°, and preferably at about 45°. This is best seen in FIG. 4, which is a cross-sectional view of the handle of the invention taken along lines 4—4 of FIG. 2. The noted angles thus correspond to angle β in FIG. 4.

The pairs of contour lines 86/88 and 50/52 lie respectively in generally perpendicular planes 75 and 77 and are spaced generally evenly about longitudinal axis 24 (FIG. 4). The lands each are of a generally inverted teardrop shape 66 as seen, for example, in FIG. 3, with the larger rounded end 68 of the teardrop 66 oriented generally toward the distal end of the central control section and the smaller, narrower rounded end 70 of the teardrop 66 oriented generally toward the proximal end of the central control section.

Lastly, a raised design 72 comprising an oval 74 with two semi-circles 76 adjacent the ends of the oval is formed on each of the lands 58, 60, 62, and 64 to provide a target for the user's thumb, as will be explained in more detail below. Other targets could be used, such as different raised line designs (e.g., lines, dots, solids or combinations of thereof) and depressions (e.g., lines, dimples, geometric shapes like circles, triangles, rectangles, etc. and combinations thereof). Also, combinations of raised designs and depressions could be used.

The distal brush section begins at peaks 44, 46, 54, and 56 with a neck 80 which curves downwardly from the peaks and flows into head 20. Head 20 is oriented in a plane generally parallel to the longitudinal axis of the handle and parallel to the plane in which contour lines 50 and 52 lie.

Figure 5:
FIG. 5 is a perspective view of the rigid base member of the handle of FIGS. 1–4.
Figure 6:
FIG. 6 is cross-sectional view of the rigid base member of FIG. 5, taken along lines 6—6 in FIG. 5.

Handle 12 is made using a rigid base member which is selectively overmolded with elastomer. The rigid base member 100, which is illustrated without elastomer overmolding in FIGS. 5 and 6, may be made from any convenient rigid material with an appropriate flex modulus, such as plastic, stainless steel, etc. Preferably, the rigid base member 100 will be made from a thermoplastic that is flexible yet durable such as polypropylene or polyethylene. Among these, polypropylene is presently preferred. Preferred elastomers include urethanes, styrene/ethylene/ butylene-styrene or SEBS elastomers (e.g. Kraton or Dynaflex, available from GLS Corporation of Cary, Ill., and metallocene elastomers (e.g., Engage, available form DuPont Dow Elastomers, L.L.C. of Freeport, Tex.) and fully vulcanized ethylene-propylene-diene-monomers in a continuous matrix of polypropylene (e.g., Santoprene, available from Advanced Elastomer Systems, L.P., of Akron, Ohio). Among these, Dynaflex is presently preferred. It is preferred that the elastomer have a Shore A hardness of less than about 60, and preferably a Shore A hardness in the range of about 5–30. Presently, a Shore A hardness of about 25 is most preferred.

Figure 7:
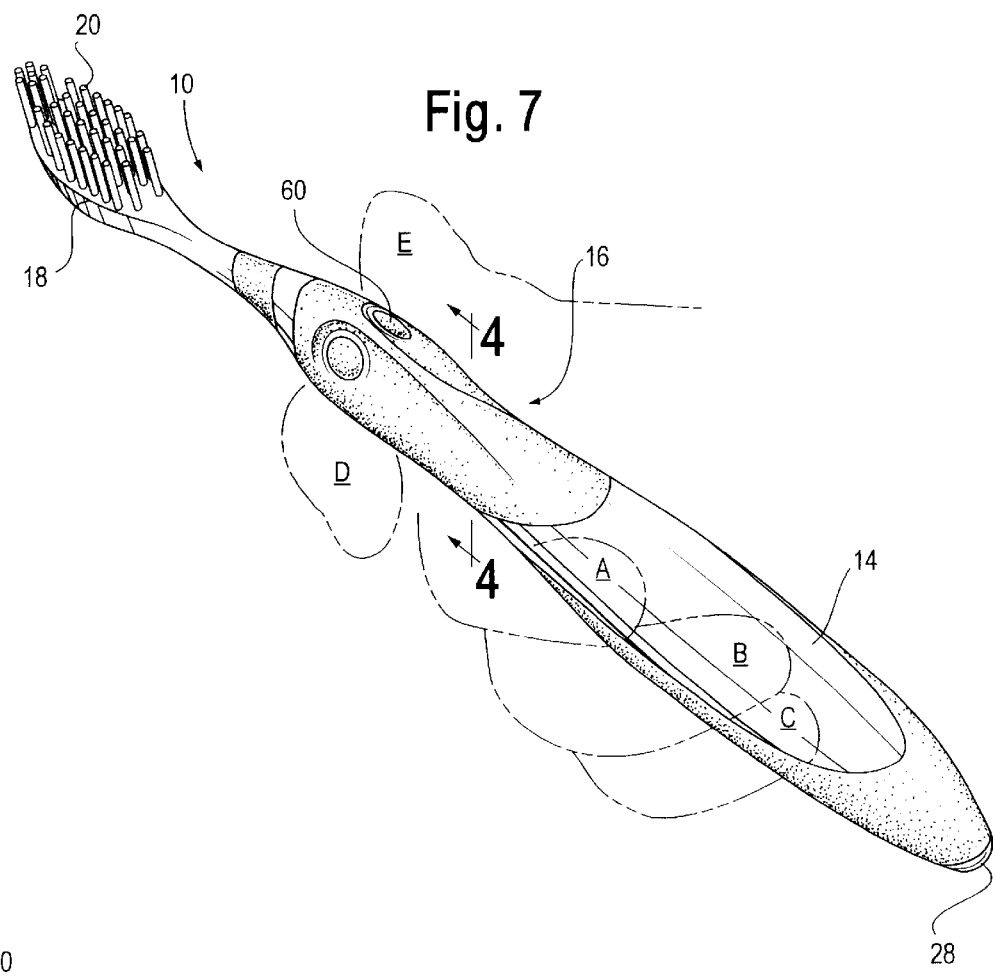
FIG. 7 is a perspective view of a handle in accordance with the present invention, shown being gripped in the hands of a user, with the contours of the user's hand shown in broken lines.

Rigid base member 100 includes an overmolding area 102 extending from just distal to the end 28 of the handle to form a slot 104 in the top of the base member that extends below the handle along its proximal and central control sections along a half-moon cut-away profile 108 flanked by a pair of ledges 110, as best seen in FIG. 7. The cut-away profile flows from the bottom of the handle into another slot 112 that encircles the neck of the distal brush section of the handle. A through-slot 114 is formed in the control section and a blind slot 116 is formed in the proximal section of the handle to help anchor the elastomer to the rigid base member.

The elastomer is selectively overmolded onto the rigid base member using conventional molding techniques, such as conventional injection molding. Preferably an elastomer will be chosen that will chemically bond to the rigid base member. Thus, the rigid base member is transferred to a cavity which generally corresponds to the rigid base member in shape, but includes mold portions corresponding to the profile of the completed handle of FIGS. 1–4. Melted elastomeric material is then injected at a location in the region of the overmolding area, whereupon the elastomer enters the overmolding area of the mold cavity to fill the cavity and form the elastomer portions of the handle, as described below.

The above design produces not only a bonding attachment when an elastomer is chosen that will chemically bond to the rigid base member, it also mechanically anchors the elastomer. The mechanical anchoring derives from the single piece of elastomer that encircles the base member as well as passes through slot 114 and enters slot 116.

In the final handle, there is elastomer at the top of the handle in the proximal grip section at 120 extending to and running along the bottom of the handle at 122 and up through the neck at 122. There is also elastomer in the central control section at 124. The remaining sections of the handle (unshaded areas) comprise exposed portions of the rigid base member that combine with the adjacent elastomer portions of the handle for comfort and aesthetic reasons. Most importantly, the lands 58–68 are covered with elastomer.

Figure 8:
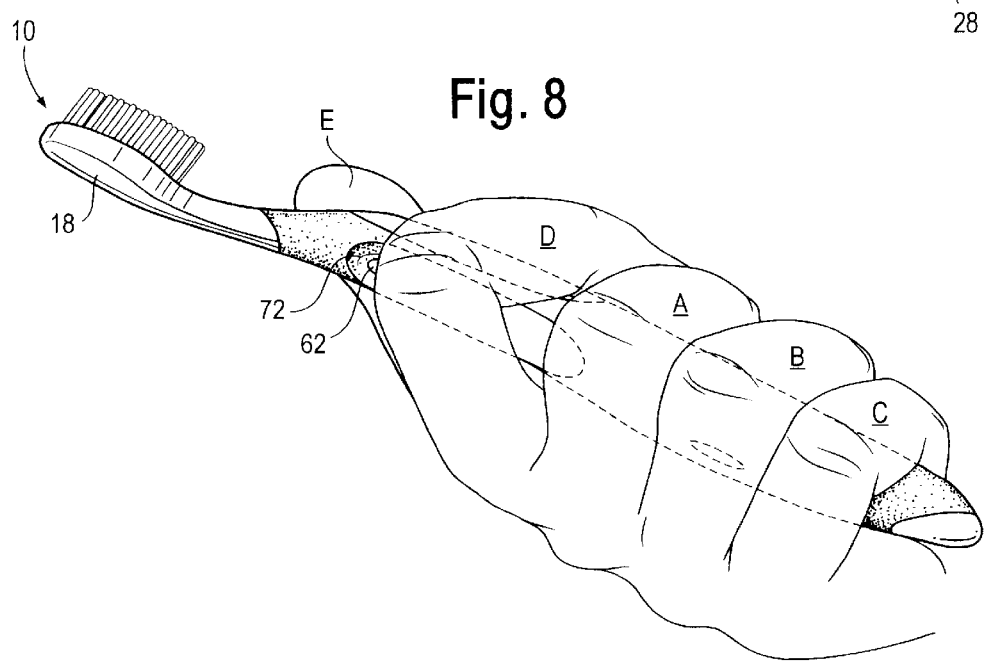
FIG. 8 is a perspective view of a handle in accordance with the present invention, shown being gripped in the hands of a user, with the contours of the proximal grip section and central control section shown in broken lines.

The use and operation of the handle of this first embodiment of the invention is illustrated in FIGS. 7 and 8. As seen first in FIG. 7, the handle is shown with the top exposed, bristles 20 pointing upwardly. The handle is resting comfortably in the user's grip with the three lower fingers A, B and C curled around and gripping ellipsoidal proximal grip section 14. Meanwhile, the central control section is held between the forefinger D and the thumb E which are pressing gently on the elastomer of opposite lands 60 and 62 just below one primary and one secondary peak. It is preferred that the handle be positioned with the thumb and forefinger at raised designs 72 on these lands, which is easily accomplished both visually and by way of the tactile feedback sensation that the user gets when the thumb and forefinger touch the raised designs.

Figure 15:
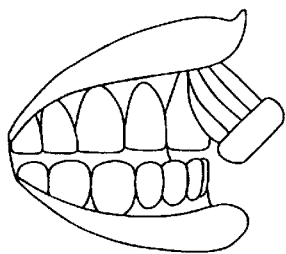
FIG. 15 is a diagrammatic representation showing the bristles of the head of the handle of FIGS. 1–3 nestled at and below the gum line of a person using the handle.

With the handle in the user's grip as described above, the hand is moved to position the brush bristles along the gum line of the teeth to be brushed, at approximately a 45° angle, with at least one row of bristles nestled at and below the gum line, as shown diagrammatically in FIG. 15. While the brush head is oriented in this way, it is gently moved back and forth in short strokes so that bristles in the gingival sulcus loosen and remove plaque present there while the rest of the bristles brush and massage the exposed surface of the gum and clean the exposed tooth surfaces. When it is desired to move the brush head to group of teeth in another quadrant, the brush head is lifted away and the user rotates the brush handle 90° or 180° along its longitudinal axis to properly position the bristles at the new location at approximately a 45° angle, with at least one row of bristles nestled at and below the gum line.

FIGS. 10 and 11 illustrate another elongated handle 200 in accordance with the invention having a hand gripping section 202 at its proximal end and an attachment section 204 at its distal end, with elastomeric over-molded areas.

The handle includes an attachment section 204 with a D-shaped recess 206 that opens into the distal end of the handle, and a release lever 208. There is also a carrying member 210 (FIG. 13) that includes an engagement portion 212 and a holder portion 214. Holder portion 214 has a generally D-shaped cross-section 216 corresponding in shape to recess 206 so that when attached, the handle and carrying member present a smooth surface from the gripping end of the handle through the cleaning or stimulating element at the distal end of the device. A dental hygiene element in the form of a cleaning or stimulating element like the interdental brush 218 of FIG. 12 will typically protrude from the carrying member.

In all embodiments, a firm mounting of the carrying member in the handle is achieved by having "D" shaped profile 216 of engagement portion 212 correspond to the profile of recess 206 and the width of the engagement portion be slightly larger than the width of the recess.

Handle 200 includes a rigid base member 240 (FIG. 13 discussed below) which may be made from any convenient rigid material with appropriate flex modulus, such as those described above in connection with the embodiment of FIGS. 1–9. Again, polypropylene is the preferred material.

Handle 200 also includes elastomeric over-molded areas including a top elastomeric portion 220, a bottom elastomeric portion 222 and a base elastomeric portion 224 near the proximal end of the handle. In the illustrated embodiment, the gripping section is wider than it is thick to help the user to tactilely sense the front and back of the handle. Preferred elastomeric materials are also as described above. Again it is preferred that the material chosen have a Shore A hardness of about 25. Additionally, both the top and bottom elastomeric portions as well as the base elastomeric portion can be provided with a series of ribs 226 oriented generally perpendicularly to the longitudinal axes of the handle to help prevent slippage of the handle in the user's hand.

As best seen in the cross-sectional view of FIG. 14, the rigid base member 240 has rounded or radiused corners 242 running along at least the length of the rigid member alongside the top and bottom elastomeric portions 220 and 222. Also, top elastomeric portion 220 and bottom elastomeric portion 222 have a generally circular profile. Elongated valleys 248, 250, 252, and 254 are formed adjacent each of the radiused corners of the rigid base member. These valleys may be best understood from FIG. 14 which shows an enlarged partial view of valley 256, radiused corner 258, a flat portion 260 and a circular portion 262. These elongated valleys provide locations in the gripping section of the handle in which the user will rest his or her fingers and thumb for accurate control of the handle. In other words, the user can comfortably roll the handle in his or her hand until the pads of the forefinger or thumb rest comfortably in one of elongated valleys 248–254 with the particular cleaning or stimulating element in place in the handle, oriented appropriately in the user's mouth.

Top and bottom elastomeric portions 220 and 222 add significantly to the comfort of using the handle since they will compress in the user's hand as his or her grip tightens. Also, the round profile of these members gives the handle a near uniform aspect ratio and contributes to the rotary movement from one elongated valley to another.

Rigid base member 240, which may be formed by conventional injection molding techniques, is illustrated in FIG. 13, before over-molding of the elastomeric portions. The rigid base member thus includes an annular slot 250 at its distal end, a longitudinal ridge 252 in the form of a depression in the bottom surface 254 of the base member and a generally elliptical cavity 256 with a generally flat bottom surface 258, also formed in the bottom surface of the base member. A similar corresponding elliptical cavity is formed in the top surface of the rigid base member, but is not shown in the figures. Finally, a slot 260 is formed in cavity 256 and in a corresponding cavity in the bottom surface of the base member.

Figure 16:
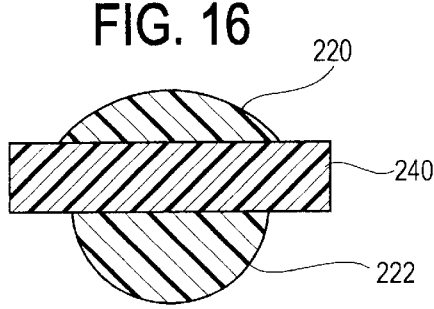
FIG. 16 is a diagrammatic cross-sectional view of an alternative embodiment of the invention.

FIG. 16 is a diagrammatic representation of the cross-sectional view of the handle of FIGS. 10–14, corresponding to the cross-sectional view of FIG. 11. This diagrammatic representation is intended to highlight the profiles of the elastomeric portions of the gripping section of the handle.

Figure 17:
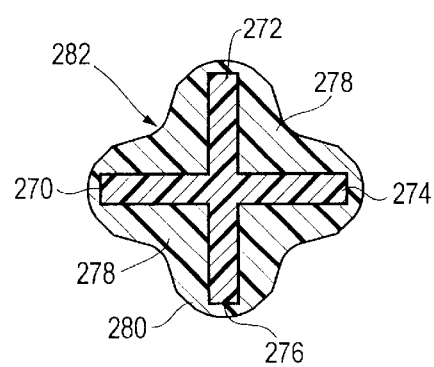
FIG. 17 is another diagrammatic cross-sectional view of an alternative embodiment of the invention.

FIG. 17 is an alternative diagrammatic cross-sectional view of another embodiment of the handle of the present invention in which the rigid base member includes four generally perpendicular elongated ribs 270, 272, 274, and 276 with elastomer 278 molded about the base member. The elastomer is molded to provide a series of upstanding portions 280 separated by a series of valleys 282. Thus, as described in connection with the embodiment of FIGS. 9–15, the user may roll the handle in the hand until the pads of the forefinger or thumb rest comfortably.

Figure 18:
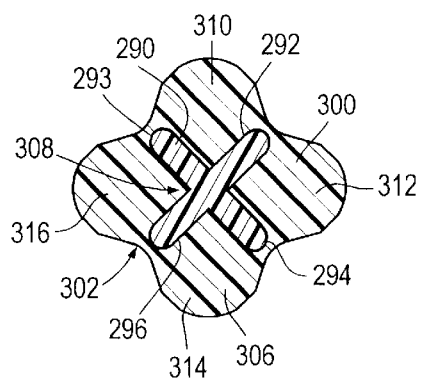
FIG. 18 is a diagrammatic cross-sectional view of an alternative embodiment of the invention.

FIG. 18 is another diagrammatic cross-sectional view of another embodiment of the handle of the invention. In this figure, the rigid base member also includes four generally perpendicular longitudinally elongated ribs 290, 292, 294, and 296, which may be generally rounded at their edges 298, as shown. Again, elastomer 300 is formed about the rigid base member. In this embodiment, however, rounded valleys 302 are formed opposite the tips 304 of the elongated ribs of the rigid base member and hills 306 are formed opposite the interstices 308 between the elongated ribs. While this design will rotate in the user's hand in a fashion similar to that of the design of FIGS. 9–16, the increased elastomeric material at 310, 312, 314, and 316 will provide substantially increased compliance and therefore a softer feel in the user's hand.

Figure 19:
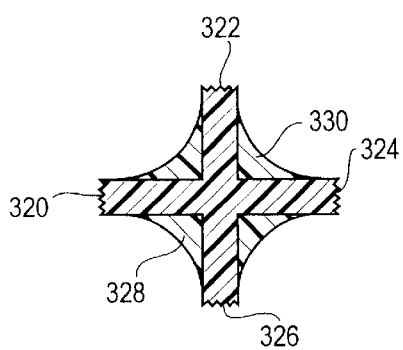
FIG. 19 is a diagrammatic cross-sectional view of an alternative embodiment of the invention.

FIG. 19 is yet another diagrammatic cross-sectional view of another embodiment of the handle of the present invention. In this design, a rigid base member corresponding to that of FIGS. 9–17 is provided, again with longitudinally elongated ribs 320, 322, 324, and 326. In this embodiment, however, the elastomeric material 328 is formed in the interstices 330 between the ribs of the base member with the edges 332 of the base member exposed. This design therefore again captures the rolling feature of the handle since it again provides four rounded elongated valleys. In this design, however, far less elastomeric material is provided producing less compliance and a less soft sensation in the user's hand coupled with the exposed tips 332 of the rigid base member which will tactilely signal to the user where the handle lies in the hand as it is rotated.

Figure 20:
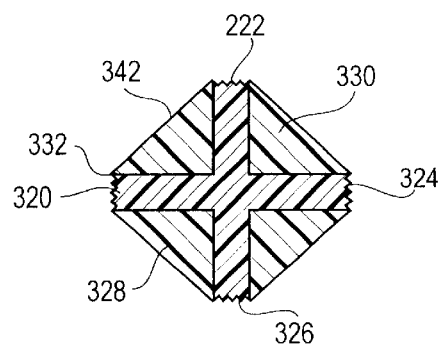
FIG. 20 is a diagrammatic cross-sectional view of an alternative embodiment of the invention.

Finally, FIG. 20 illustrates yet another diagrammatic cross-sectional view of the handle of the invention. This design corresponds to that of FIG. 19, but for the provision of additional elastomeric material 340 between the longitudinally elongated ribs 320, 322, 324, and 326 of the base member which are provided with flat surfaces 342. These flat surfaces, although presently less preferred than the rounded surfaces discussed above, yield substantially more than the edges 332 of the legs of the rigid base member effectively softening the sensation of valleys between the legs as the handle is rotated and squeezed by the user while being gripped.

While the present invention is described above in connection with specific embodiments, the invention is intended to cover all alternatives, modifications or equivalents that may be included within its sphere and scope, as defined by the appended claims.

What we claim is:

1. A dental hygiene system handle well adapted for comfortable gripping, manipulating, and rotating about its longitudinal axis by a user comprising:

a generally ellipsoidal proximal grip section with a distal brush section, and a central control section located therebetween, the central control section necking down and then diverging outwardly in a smooth curved contour to a pair of peaks near the distal end of the control section, and the central control section including two pairs of elastomeric lands on opposite sides of the central control section, one of each pair of lands for receiving the thumb of a user and the other of each pair of lands for receiving the forefinger of a user.

2. The dental hygiene system handle of claim 1 in which the handle includes a toothbrush head with bristles at its distal end.

3. The dental hygiene system handle of claim 2 in which the handle is unitary, the toothbrush head being integral with the rest of the handle and the bristles being mounted in the head.

4. The dental hygiene system handle of claim 2 in which the toothbrush head is removably mounted to the handle.

5. The dental hygiene system handle of claim 1 in which the proximal grip section is generally ellipsoidal in shape.

6. The dental hygiene system handle of claim 5 in which the ellipsoidally shaped proximal grip section is rounded at its proximal tip and bulges outwardly as the contour of the grip moves distally to its maximum radial divergence.

7. The dental hygiene system handle of claim 1 in which the lands meet each other at the outer surface of the central control section at angles from about 25° to 65°.

8. The dental hygiene system handle of claim 1 in which the lands meet each other at the outer surface of the central control section at an angle of about 45°.

9. The dental hygiene system handle of claim 1 in which the lands include a raised design.

10. The dental hygiene system handle of claim 1 in which the handle comprises a rigid base member that is selectively overmolded with elastomer.

11. The dental hygiene system handle of claim 10 in which the rigid base member is made from polypropylene.

12. The dental hygiene system handle of claim 10 in which the elastomer has a Shore A hardness of about 25.

13. The dental hygiene system handle of claim 1 including elastomer at the top of the handle in the proximal grip section extending to and running along the bottom of the handle, and elastomer in the central control section.

14. The dental hygiene system handle of claim 13 in which the remaining sections of the handle comprise exposed portions of the rigid base member.

15. The dental hygiene system of claim 1 including an attachment section with a D-shaped recess that opens into the distal end of the handle, a release lever, and a carrying member having an engagement portion that fits in the recess.

16. The dental hygiene system of claim 15 in which the carrying member includes a dental hygiene element.

17. A dental hygiene system handle well adapted for comfortable gripping, manipulating, and rotating about its longitudinal axis comprising:
a handle having a rigid base member that is selectively overmolded with elastomer, the handle having aproximal grip section, a distal brush section, and a central control section located therebetween,
the central control section including elastomeric lands for receiving the thumb and forefinger of a user on opposite sides of the central control section,
in which a through-slot is formed in the control section and a blind slot is formed in the proximal section of the handle to help anchor the elastomer to the rigid base member.

18. A dental hygiene system handle well adapted for comfortable gripping, manipulating, and rotating about its longitudinal axis comprising:
a handle having a rigid base member that is selectively overmolded with elastomer, the handle having a proximal grip section, a distal brush section, and a central control section located therebetween,
the central control section including four elastomeric lands for receiving the thumb and forefinger of a user on opposite sides of the central control section, and
the rigid base member including an overmolding area extending from just distal to the end of the handle comprising a slot in the top of the base member that extends below the handle along its proximal and central control sections to form a half-moon cut-away profile on the bottom of the rigid base member.

19. The dental hygiene system handle of claim 18 in which the half-moon cut-away profile is flanked by a pair of ledges.

20. The dental hygiene system handle of claim 18 in which the cut-away profile runs from the bottom of the handle into another slot that encircles in the neck of the distal brush section of the rigid base member.

21. A dental hygiene system handle well adapted for comfortable gripping, manipulating, and rotating about its longitudinal axis by a user comprising:
a proximal grip section, a distal brush section, and a central control section located therebetween,
the central control section including two pairs of elastomeric lands on opposite sides of the central control section, one of each pair of lands for receiving the thumb of a user and the other of each pair of lands for receiving the forefinger of a user,
the lands being of a generally inverted teardrop shape, with a larger rounded end of the teardrop oriented generally toward the distal end of the central control section and a smaller, narrower rounded end of the teardrop oriented generally toward the proximal end of the central control section.

22. A dental hygiene system handle including a rigid base member with four generally perpendicular elongated ribs and elastomer molded therebetween to provide a series of upstanding rigid portions separated by a series of elastomeric valleys.

23. The dental hygiene system of claim 22 in which the four generally perpendicular longitudinally elongated ribs are rounded at their edges, and rounded valleys are formed opposite the tips of the elongated ribs of the rigid base member with hills formed opposite the interstices between the elongated ribs.

24. The dental hygiene system of claim 23 in which the elastomeric material is formed in the interstices between the ribs of the base member with the edges of the base member exposed.

* * * * *